United States Patent [19]
Choi et al.

[11] Patent Number: 5,593,856
[45] Date of Patent: Jan. 14, 1997

[54] METHOD FOR PRODUCING PROTEIN IN A CELL-FREE SYSTEM

[75] Inventors: Cha-yong Choi, 223-1301, Olympic Family Apt., 150, Munjeong 2-dong Songpa-gu; Dong-myung Kim; Gyoo-yeol Jung, all of Seoul, Rep. of Korea

[73] Assignee: Cha-yong Choi, Seoul, Rep. of Korea

[21] Appl. No.: 296,230

[22] Filed: Aug. 25, 1994

[30] Foreign Application Priority Data

May 4, 1994 [KR] Rep. of Korea ................. 94-9850
Jul. 25, 1994 [KR] Rep. of Korea ............... 94-17978

[51] Int. Cl.$^6$ ............................................. C12P 21/00
[52] U.S. Cl. ................................... 435/68.1; 435/69.1
[58] Field of Search .......................... 435/68.1, 69.1; 530/413

[56] References Cited

U.S. PATENT DOCUMENTS 5,324,637  6/1994  Thompson et al. ................ 435/68.1

OTHER PUBLICATIONS

Eckert et al., *Animal Physiology*, W. H. Freeman & Co., NY, 1983, p. 274.
Endo et al., J. Biotechnol. 25:221–230 (1992).
Kigawa et al., J. Biochem. 110:166–168 (1991).
Nakano et al., Biosci. Biotech. Biochem. 58:631–634 (1994).
Yoshizawa et al., Nucleic Acids Res. 22:2217–2221 (Jun. 1994).
Millipore 1992/1993 Pharmaceutical Process Filtration Catalog, Millipore Corp., Marlborough, MA.

*Primary Examiner*—Charles L. Patterson, Jr.
*Assistant Examiner*—Eric Grimes
*Attorney, Agent, or Firm*—Foley & Lardner

[57] ABSTRACT

A method for producing protein in a cell-free system uses cell-free extract required for protein production, extracted from a biological cell. According to the present invention, a wide range of proteins can be produced economically and efficiently even in a semi-continuous operation mode, by regenerating energy source, increasing operation time of the reactor with porous solid material and using selective protein isolating means having high specific affinity to a desired protein. Thus, problems appearing in the living cell (in vivo) system due to the absence of post-translational processing can be avoided and the total production amount can be greatly increased due to prolonged operation time of the reactor and increased protein productivity.

10 Claims, 2 Drawing Sheets

<PRODUCTION PROFILE IN A CONTINUOUS OPERATION MODE IN A CELL-FREE SYSTEM>

<PRODUCTION PROFILE IN A CONTINUOUS OPERATION MODE IN A CELL-FREE SYSTEM>

<PRODUCTION PROFILE IN SEMI-CONTINUOUS OPERATION MODE IN A CELL-FREE SYSTEM>

METHOD FOR PRODUCING PROTEIN IN A CELL-FREE SYSTEM

BACKGROUND OF THE INVENTION

The present invention relates to a method for producing a protein in a cell-free system, and more particularly, to a method for producing a wide range of proteins used in industrial fields related to pharmaceuticals, food, agricultural chemicals, environmental products and commodity products, in a cell-free system.

Generally speaking, there are two methods for producing protein: via a chemical process and via a biological process. In the case of producing a peptide with few amino acids, a chemical process is mainly used. Particularly, for peptides having ten or fewer amino acids, the chemical process is known to be more economical than the biological process.

Conventionally, protein production by the biological process is accomplished in an in vivo system using a genetically manipulated biological cell. Here, according to the excretion characteristics of the protein, that is, whether it is an intracellular protein or an extracellular protein, one or the other of two methods is used. In one method, an intracellular protein is produced by a method comprising the steps of culturing a cell in a proper medium to accumulate a desired protein in the cell, harvesting the cell at the appropriate growth stage of the cell, rupturing the cell and finally isolating and purifying the desired protein. In another method, an extracellular protein is produced by culturing a cell in a proper broth medium, separating cultural broth without the cell, and isolating and purifying a desired protein.

Such a biological process based on biological cells in a living state has several problems in view of protein over-production by the living biological cells and isolation and purification of a desired protein.

Generally, protein is degraded or modified by several enzymes synthesized with the growth of the cell. After synthesis, protein is frequently modified into undesired forms due to post-translational processing such as deamination or oxidation. It is very difficult to incorporate modified or unnatural amino acids into protein. Also, cytotoxic proteins inhibit the growth of the cell.

The over-production of protein beyond a predetermined concentration is also difficult to obtain because the expression of a gene coding a desired protein may be regulated by the concentration thereof. Even though an artificially mutated cell capable of over-producing the desired protein is used, there is a limitation in producing protein due to the inherent characteristics of the biological cell itself. That is, the concentration of protein accumulated in the cell or excreted into a broth generally affects the viability of the cell. Accordingly, it is very difficult to harmonize the conditions of protein over-production and cell growth, so that over-production of the desired protein is very difficult to obtain.

In an isolation and purification process, many kinds of protein are insoluble or unstable, and are either degraded by intracellular proteases or aggregate in inclusion bodies, so that the loss rate of the desired protein is generally high during protein purification, and particularly, the isolation of membraneous protein is highly complex and difficult. Also, in the case of protein used in protein products such as pharmaceuticals and food, great caution should be taken in order to prevent contamination by infecting agents or endotoxins. Therefore, the efficiency of isolation and purification of the desired protein is poor and the specific production rate and the overall productivity of the protein are both low, so that the price of the protein is considerably high.

In order to solve the above problems appearing in the in vivo system, a method for producing protein in a cell-free system, that is, an in vitro system based on a cell-free extract. However, according to a method using a conventional batch system, the required amount of mRNA is high, the length of an operation cycle is less than one hour, the basic activity of the cell-free extract is very low, and disadvantages due to enzymes degrading nucleic acids or protein are still serious. Further, it is difficult to prevent inhibition caused by energy sources, products or byproducts. Thus, protein productivity remains very low.

In order to solve the above problems caused by the batch process, Alexander S. Spirin et al. have suggested a method of cell-free translation for producing protein using a continuous system (see "A Continuous Cell-free Translation System Capable of Producing Polypeptides in High Yield," *Science*, Vol. 242, 1988, pp 1162–1164). Using this system, protein synthesis is maintained at a constant rate for more than twenty hours, but the productivity was only about 5 pmol/pmol mRNA. Subsequently, a coupled transcription-translation process with a continuous system was suggested by Vladimir I. Baranov et al. (see "Gene expression in a cell-free system on the preparative scale," *Gene*, Vol. 84, 1989, pp 463–466). This system worked at a constant rate for tens of hours with protein productivity of 4 µg/ml per hour, resulting in production of preparative amounts of protein. Protein produced in this system was identified by autoradiography after electrophoresis. Such research as above has concentrated on extending the period of protein synthesis but not on increasing the rate of protein synthesis.

However, it is very important to shorten the period to yield products, particularly in the cell-free protein synthesis, considering unstable substrates used in the system, such as nucleotide triphosphates and mRNA. In the case of using a membrane, an efficient mixing is inhibited according to the density increase of the reaction mixture with operation time. Further, flow is perpendicular toward the membrane so that a "plugging" phenomenon is frequently generated and thus operation does not continue functioning properly beyond 100 hours.

Further, Hideo Nakano et al. have suggested a method for increasing the rate of protein synthesis in the cell-free system using a cell-free extract concentrated by an ultrafiltration membrane (see "An Increased Rate of Cell-free Protein Synthesis by Condensing Wheat-germ Extract with Ultrafiltration Membranes," *Bioscience, Biotechnology, Biochemistry*, Vol. 58(4), 1994, pp 631–634). According to this system, the protein productivity was about 30 µg/ml per hour, which is five-fold that obtained by the above continuous-flow cell-free (CFCF) system, but the final amount of synthesized protein was one third of that obtained by the CFCF system and operation time was only six hours.

As shown from the above, both protein productivity and production amount are still low, which is an obstacle in implementing the industrialization of cell-free protein synthesis. Therefore, improvements are greatly required in terms of the total productivity of the protein by increasing the specific production rate and the length of system operation, and in terms of a cost-reduction by regenerating an expensive energy source in order to recycle the regenerated energy source.

SUMMARY OF THE INVENTION

It is an object of the present invention to provide a method for producing protein in a cell-free system improving both protein productivity and operation length of the system.

Another object of the present invention is to provide a method for producing protein economically in a cell-free system by regenerating energy sources consumed in the protein synthetic reaction with an energy regenerating means and recycling the regenerated energy sources.

Still another object of the present invention is to provide a method for obtaining a desired protein effectively by increasing the recovery rate of the protein produced in the reactor through a protein isolating means having high adsorption specificity to the desired protein, in the method for producing protein in the cell-free system.

To accomplish the first object, there is provided a method for producing protein in a cell-free system, comprising the steps of:

preparing a cell-free extract required for synthesizing a desired protein by culturing a biological cell, rupturing the cultured cell, and extracting a cell-free extract including organelles required for protein synthesis;

supplying the cell-free extract together with a reaction medium comprising a genetic source, adenosine triphosphate and guanosine triphosphate as a first energy source for synthesizing protein, at least one second energy source for in situ regenerating the first energy source selected from a group consisting of high-energy phosphate compound, carbohydrate and their derivatives, amino acids as a substrate, and a porous solid material, with a membrane-type protein synthesis reactor; and operating the reactor to produce a desired protein.

To accomplish the second object, there is also provided a method for producing protein in a cell-free system, further comprising the steps of regenerating the first energy source consumed in the protein synthetic reaction and recycling the regenerated energy source by providing a separate energy regenerating means connected with the reactor in the cell-free system.

To accomplish the third object, there is also provided a method for producing protein in a cell-free system, further comprising the step of isolating the desired protein from the reaction mixture by providing a separate protein isolating means, for selectively isolating only the desired protein, connected with the reactor in the cell-free system.

BRIEF DESCRIPTION OF THE DRAWINGS

The above objects and other advantages of the present invention will become more apparent by describing in detail preferred embodiments thereof with reference to the attached drawings in which.

DETAILED DESCRIPTION OF THE INVENTION

Figure 1:
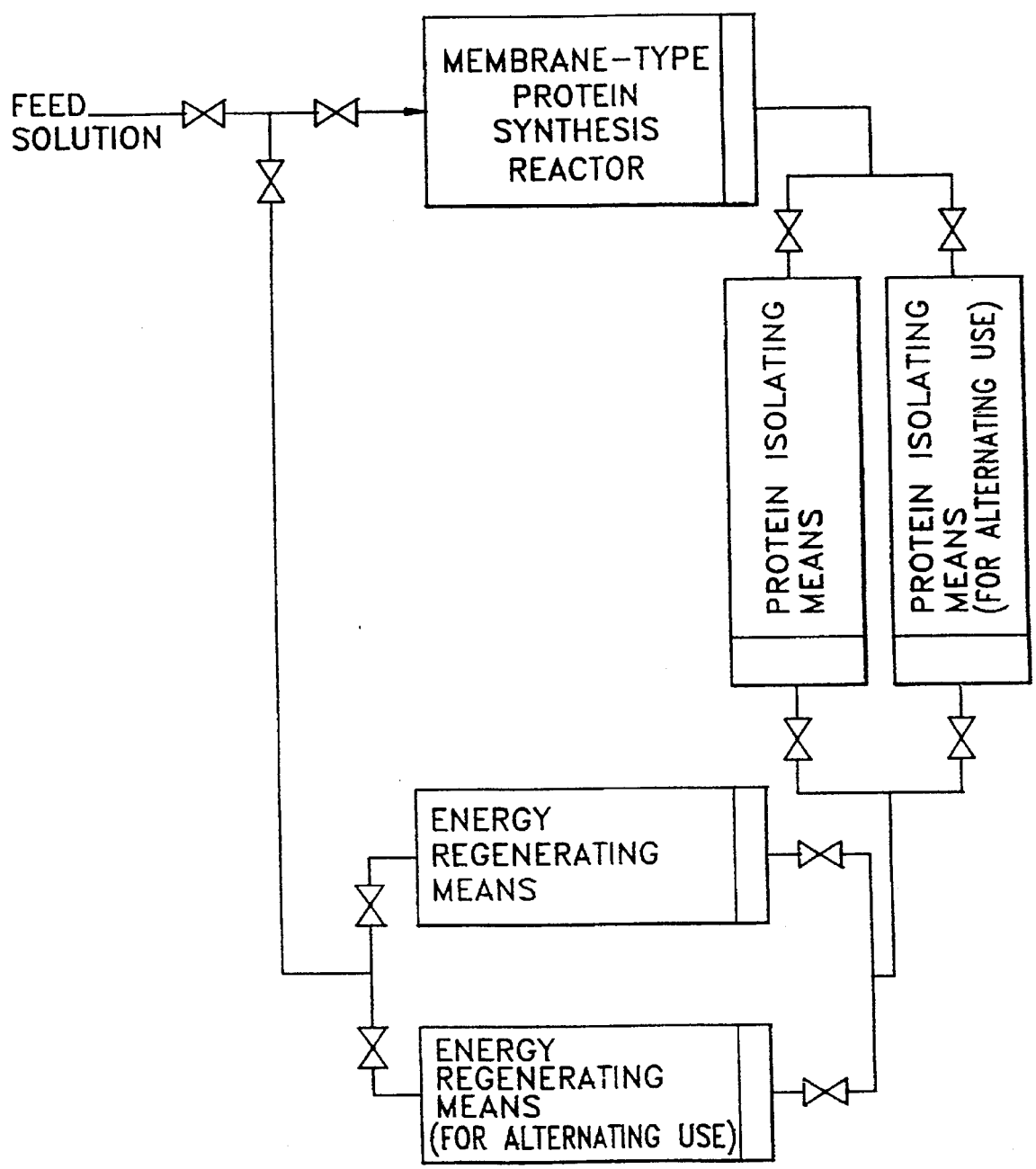
FIG. 1 is a block diagram illustrating the structure of a cell-free system comprising the protein synthesis reactor, energy regenerating means and protein isolating means for carrying out the method according to the preferred embodiment of the present invention.

According to one embodiment of tile present invention, the cell extract is prepared from a cell having a good activity of protein synthesis, selected among microorganic cells such as Escherichia or Bacillus, plant cells such as a wheat germ cell, rice germ cell or barley germ cell, and animal cells such as a CHO (Chinese hamster ovary) cell, hybridoma cell or reticulocyte. The cell extract may be prepared by culturing the cell, and rupturing the cultured cell, removing inhibitory extract using an ultrafiltration membrane. Also, the specific production rate of protein can be greatly increased by adding polyethylene glycol to the cell-free extract, and removing the precipitates before the concentrating step using the ultrafiltration membrane. At this step of preparing the cell-free extract, a cell which is genetically manipulated so as not to produce protease, nuclease nor phosphatase may be used. Also, tRNA as an essential component for producing protein may be used in the form included in the cell-free extract without further addition, or it may be added to the reactor in a form other than that included in the cell-free extract.

Preferably, as the genetic source, DNA and/or mRNA to a specific protein may be used in proper combination, depending on the operation type of the reactor, such as DNA-mRNA coupling, mRNA replication-translation coupling and non-coupling translation. That is, it is sufficient to provide only mRNA to the specific protein with the reactor when the reactor is operated in the non-coupling translation type. However, DNA and mRNA to the specific protein and RNA monomers such as ATP, GTP, CTP and UTP together with necessary enzymes comprising an RNA polymerase, are provided with the reactor when the reactor is operated in the coupled transcription-translation type. In order to inhibit the activity of nucleic acid degrading enzymes, an oligo deoxynucleotide having a specific Sequence may be bonded at the 3' terminal of mRNA by conventional physical or chemical processes, or oxygen atoms bound to phosphate group of mRNA are partly replaced by sulfur atoms.

Preferably, as the first energy source, ATP and GTP are used. The second energy source is used for in situ regenerating the first energy source consumed in the protein synthetic reaction, that is, from ADP and GDP to ATP and GTP. The second energy source includes high-energy phosphate compounds, carbohydrates and their derivatives. Here, a specific kinase that is determined depending on the second energy source, succinyl coenzyme A, a synthetic enzyme of succinyl coenzyme A and/or succinylthiokinase may also be used. The high-energy phosphate compounds and their derivatives include phosphoenolpyruvate, phosphocreatine, acetylphosphate and polyphosphate. If α-keto glutarate is used as the carbohydrate for regenerating the first energy source, NADH generated in tiffs reaction may be used for producing lactate from pyruvate or other useful reactions.

The surface area of the porous solid material and the size and structure of the pore are all variable. Also, physiochemical properties comprising acidity/basicity of the surface are variable. A porous solid material having a diameter of 0.1–1,000 μm, a surface area of 10–1,000 $m^2$/gr, and a granule, plate or honeycomb shape is preferred. The porous solid material preferably includes polymeric materials and inorganic oxides. Preferred polymeric materials are porous chitosan, porous cellulose, porous gelatin, porous collagen and their derivatives, and porous metallic compounds. Preferred inorganic oxides are alumina, silica, titania, zirconia, molybdena, vanadium oxide, cobalt oxide and their mixtures, and various kinds of zeolites. In addition to these, compounds doped with various kinds of inorganic compounds or modified by various organic materials, may be used. According to another embodiment of the present invention, protein synthetic reaction is improved by using the porous solid material. That is, protein production rate is greatly increased, the plugging of the membrane is decreased significantly, and total operation time is highly increased, to obtain a good protein productivity and large production amount by using the porous solid material.

In addition to the above components such as cell-free extract, genetic source, amino acids, first and second energy sources and porous solid material, materials required for protein synthesis may be added to the reactor. These materials include salt, polymeric compound having ionic group, cAMP, inhibitors for protein or nucleic acid degrading enzymes, inhibitor for regulator of protein synthesis, oxidation/reduction adjuster, non-denaturing surfactant, buffer component, spermine, spermidine and kinase.

The salt preferably includes potassium, magnesium, ammonium and manganese salt of acetic acid or sulfuric acid, and some of these have amino acids as a counter anion.

The polymeric compounds having ionic group are preferably polyethylene glycol, dextran, diethyl aminoethyl, quaternary aminoethyl and aminoethyl.

The oxidation/reduction adjuster is preferably dithiothreitol, ascorbic acid, glutathione and/or their oxides. Also, a non-denaturing surfactant such as Triton X-100 may be used at a concentration of 0–0.5 molar.

Preferably, spermine and spermidine may be used for improving protein synthetic ability, and cAMP may be used as a gene expression regulator. Conventionally, neither spermine nor spermidine have been used when using polyethylene glycol, but the proper combination usage of these three compounds results in a synergistic effect toward protein synthesis in the present invention.

When changing the concentration of a particular component of the reaction medium, that of another component may be changed accordingly. For example, the concentrations of several components such as nucleotides and energy source compounds should be simultaneously controlled in accordance with the change in those of other components. Also, the concentration levels of components in the feed solution to the reactor may be varied over time. For example, amino acid concentration in the feed solution may be increased after several hours of continuous operation. Polyethylene glycol and porous solid material may be used at a concentration of 0–10%.

The membrane provided with the reactor includes any membrane regardless of its physical properties, such as ionic or non-ionic, hydrophilic or hydrophobic, and polar or non-polar.

The reactor is preferably run in any type such as batch, extended batch, semi-batch, semi-continuous, fed-batch and continuous, and more preferably, it may be selected in accordance with application purpose.

Preferably, the reactor is maintained in the range of pH 5–10 and a temperature of 20°–50° C., and more preferably, in the range of pH 6–9 and a temperature of 25°–40° C.

The direction of liquid flow can be perpendicular and/or tangential to the membrane. Tangential flow is effective for recycling the first energy source and for preventing membrane plugging and is superimposed on perpendicular flow. Flow perpendicular to the membrane may be caused or effected by a positive pressure pump or a vacuum suction pump.

When using a protein isolating means in a continuous operation mode, the product output from the reactor through a membrane flows into the protein isolating means. In a semi-continuous operation mode, the outside or outer surface of the membrane is put into contact with predetermined solutions that are cyclically changed in a predetermined order. These solutions contain substrates such as amino acids and nucleotide, in addition to components including adsorbent with high specific affinity to the inhibitor of the protein synthesis. At this time, the reactor is operated in dialysis, diafiltration batch or fed-batch mode. A feed solution may be supplied to the reactor through the same membrane or a separate injection unit. Here, synthesized protein is accumulated in the reactor, and then is isolated and purified according to the usual method for protein purification after completion of the system operation.

The solution in contact with the outside surface of the membrane may be cyclically changed, and may be in a steady tangential flow with respect to the membrane. The reactor may be stirred internally or externally by proper agitation means.

When using a separate energy regenerating means, mitochondria together with high-energy compounds such as carbohydrate, organic acid, aldehyde and alcohol, and necessary enzymes, or photosynthetic organelles such as chromatophore or chloroplast together with light energy may be used. Energy regenerating means may be provided with a membrane having pores of proper size and ionic characteristics. Photosynthetic organelles used for energy regenerating means may be derived from plants or microorganisms.

During protein synthesis in the reactor, the protein isolating means for selectively isolating the desired protein may include a unit packed with particles coated with antibody molecules or other molecules immobilized with a component for adsorbing the synthesized, desired protein, and a membrane with pores of proper sizes. Preferably, the protein isolating means comprises two columns for alternating use.

When both protein isolating means and energy regenerating means are used, synthesized protein may be selectively adsorbed into the protein isolating means with high specific affinity to the desired protein, and remaining components may be sent to the reactor through the energy regenerating means.

According to the block diagram as shown in FIG. 1, the product of the reactor may be directed to one of the protein isolating means consisting of two columns. The two columns are for alternative use for continuous operation of the overall cell-free system. Also, if the system further comprises energy regenerating means, effluent from the protein isolating means may be sent to the reactor through the energy regenerating means. As described above, the protein isolating means and energy regenerating means in the cell-free system as shown in FIG. 1 may be optionally used, and the connection between them may be varied.

The identification of the protein produced in the reactor may be performed by electrophoresis, and then autoradiography (identification of leu-$C^{14}$ incorporated into the synthesized protein by using $C^{14}$-labelled leucine as one of the amino acid substrate) for identifying a trace amount of protein, and Coomassie blue staining for identifying a relatively large amount of protein may be performed according to the amount of the protein. Also, quantitative analysis for the synthesized protein may be performed by a usual method such as the Lowry method.

The present invention will be described in detail, with reference to drawings attached hereto, by way of the following examples which are merely representative and illustrative of the present invention and are in no way to be considered as limiting the invention to the specific examples.

EXAMPLE 1

Preparation of Cell-free Extract

A seed culture was performed in a usual liquid broth medium by inoculation with an overnight culture of E. coli. The seed culture broth was inoculated into a five-liter fermenter including 75 mM of potassium acetate, 1% of yeast extract, 5% of glucose and 0.05% of vitamin. The overnight culture was performed at 30° C. Then, cells were harvested and disrupted by a usual method such as through a French press or ultrasonicator. The resultant lysate was centrifuged at 30,000 g, for five minutes at 4° C. and supernatant was dialyzed against the Tris buffer (pH 7.6). Organic material such as polyethylene glycol was added to the dialyzed extract in its final concentration of 5%, and then the supernatant was concentrated by pressure filtration through ultra filtration membrane to obtain cell-free extract to be used for producing protein in the cell-free system.

EXAMPLE 2

Protein Production in a Continuous Operation Mode

Figure 2:
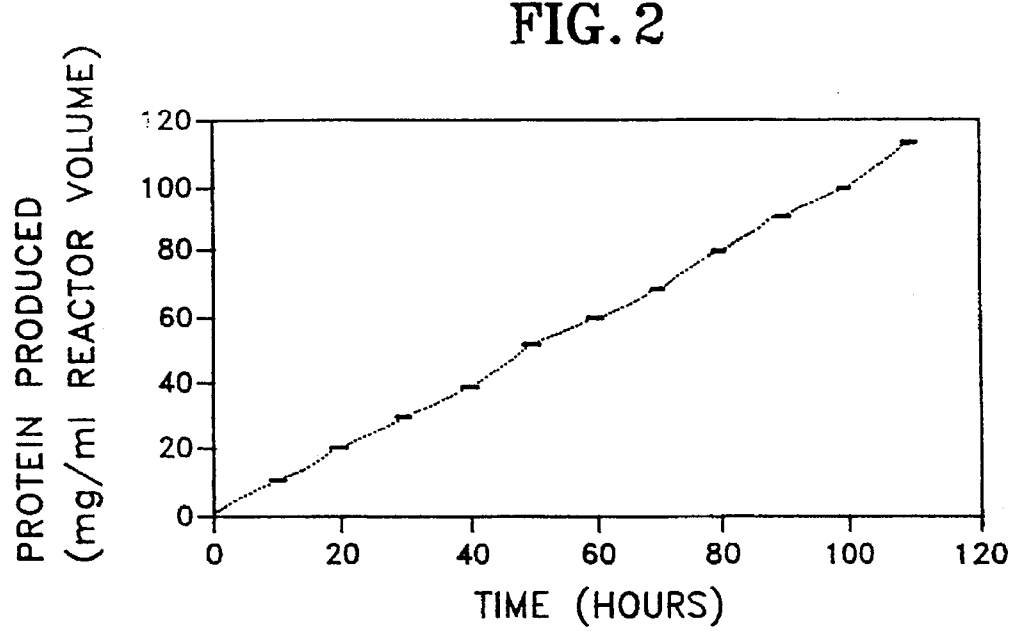
FIG. 2 is a graph showing the amount of protein produced in a continuous operation mode versus operation time in a cell-free system, according to one embodiment of the present invention.

To a membrane type protein synthesis reactor, reaction medium was added together with a predetermined concentration of cell-free extract obtained from Example 1, comprising 2.6 mM of ATP, 0.8 mM of GTP, 1 mM of twenty different amino acids, 210 mM of potassium acetate, 80 mM of ammonium acetate, 16 mM of magnesium acetate, 0.67 mM of cAMP, 2 mM of dithiothreitol, 24 mM of phosphoenol pyruvate, 12 µg/ml of PEP kinase, 2 g/l of polyethylene glycol, 3 g/l of alumina, mRNA, 50 mM of Tris acetate buffer (pH 7.6) and other materials required for protein synthesis. Operation in the continuous mode was maintained by supplying feed solution to the reactor at the flow rate of 1 VVH. The temperature and pH of the reactor were maintained at 37° C. and 7.6, respectively, and a moderate agitation was performed internally. The protein produced continuously in the reactor was identified by autoradiography and Coomassie blue staining after electrophoresis. The quantitative analysis was performed by the Lowry method to give the results shown in FIG. 2. In the graph of FIG. 2, the X-axis represents operation time of the continuous operation mode, and the Y-axis represents total amount of protein produced per milliliter of the volume of the reactor. As shown in the graph, operation was maintained more than 120 hours, and the average yield of protein at that time was about 2 mg/ml per hour.

EXAMPLE 3

Protein Production in a Semi-continuous Operation Mode

Figure 3:
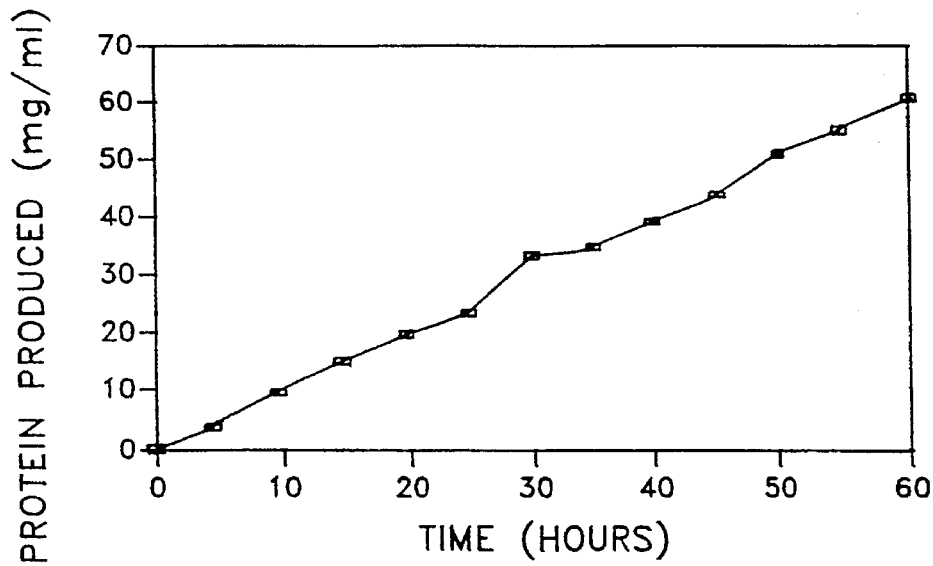
FIG. 3 is a graph showing the amount of protein produced in a semi-continuous operation mode versus operation time in a cell-free system, according to another embodiment of the present invention.

The same procedure as in Example 2 was repeated except that the operation of the cell-free system was performed in a semi-continuous operation mode to give the results FIG. 3.

In the semi-continuous operation mode, operation was maintained for more than 50 hours, and the total amount of protein was about 60 mg/ml.

EXAMPLE 4

Addition Effect of Porous Solid Material

The same procedure as in Example 3 was repeated except that alumina as a porous solid material was added to the reactor with variable concentrations, to give the results shown in Table 1. Here, the operation time was increased significantly.

TABLE 1

| concentration of porous solid material (mg/ml) | 10 | 20 | 30 | 40 | 50 |
|---|---|---|---|---|---|
| protein productivity (mg/ml/h) | 0.6 | 0.8 | 1.2 | 0.9 | 0.7 |

As shown in Table 1, the maximum productivity of protein was obtained at a concentration of 30 mg/ml of alumina. The porous solid material is assumed to have functions to improve the protein synthetic reaction itself and to prevent plugging of the membrane.

EXAMPLE 5

Addition Effect of Polyethylene Glycol

The same procedure as in Example 3 was repeated except that polyethylene glycol was added to the supernatant at a final concentration of 2% in the step of preparing the cell-free extract in Example 1. Also, for comparison, the same procedure was repeated using a cell-free extract obtained without addition of polyethylene glycol. As shown in Table 2, the protein productivity was increased dramatically with the addition of polyethylene glycol.

TABLE 2

|  | protein productivity (mg/ml/h) |
|---|---|
| with the addition of polyethylene glycol | 1.2 |
| without the addition of polyethylene glycol | 0.6 |

EXAMPLE 6

Regeneration of Energy Source

A chromatophore separated from a disrupted photosynthetic microorganism, Rhodospirillum rubrum, was used for regenerating ATP from ADP. The quantitative analysis of the nucleotide phosphate was performed by a usual method to give the results shown in Table 3.

TABLE 3

|  | ADP | ATP |
|---|---|---|
| inlet concentration (mM) | 2.2 | 0.2 |
| outlet concentration (mM) | 1.6 | 0.8 |

EXAMPLE 7

Selective Isolation of a Desired Protein

For selective isolation of a desired protein, two columns were prepared, the stationary phase of which consisted of particles chemically immobilized with an antibody (monoclonal or polyclonal) to the protein. The two columns were connected with the reactor such that, after reaching a break-through point with respect to one column, product from the reactor was directed to another column, while protein from the protein-adsorbed (saturated) column which previously reached the break-through point was eluted and then regenerated. In this manner, the overall continuity of the system was maintained by the alternating use of two columns. The operation data of the protein isolating columns is shown in Table 4.

TABLE 4

| volume of column (cm$^3$) | 100 | 200 | 300 | 400 |
|---|---|---|---|---|
| break-through time (h) | 3.1 | 6.3 | 9.3 | 12.1 |

Here, the break-through point is the time (in hours) required to saturate an affinity column with a particular component having a specific affinity with respect to the column, that is, until the particular component appears at the outlet of a column from the inlet of the column.

According to the method for producing protein in a cell-free system of the present invention, it is possible to avoid undesirable modifications appearing in a living cell (in vivo) system due to the absence of post-translation processing, and several problems caused by proteins toxic to a host cell, so that protein products such as insulin, human growth hormone, α-interferon and other vaccines can be produced effectively. Also, the total production mount as well as the specific production rate of the protein can be greatly increased compared with conventional methods by recycling the regenerated energy source, increasing operation time of the reactor with porous solid material and using selective protein isolating means having high specific affinity to a desired protein, so that protein production can be performed economically and efficiently, regardless of the number of amino acids per peptide chain.

While the present invention has been particularly shown and described with reference to particular embodiments thereof, it will be understood by those skilled in the art that various changes in form and details may be effected therein without departing from the spirit and scope of the invention as defined by the appended claims.

What is claimed is:

1. A method for producing protein in a cell-free system, comprising the steps of:

preparing a cell-free extract for synthesizing a desired protein by culturing a biological cell, rupturing the cultured cell, and extracting a cell-free extract;

supplying the cell-free extract with a reaction medium comprising (i) a genetic source, (ii) adenosine triphosphate and guanosine triphosphate as a first energy source for synthesizing protein, (iii) a phosphate compound as a second energy source for in situ replacement of the first energy source, (iv) amino acids as a substrate, (v) a porous solid material, wherein the porous solid material has a diameter ranging from 0.1 μm to 1,000 μm and a surface area ranging from 10 m$^2$/g to 1,000 m$^2$/g; in a protein synthesis reactor comprising a membrane; and operating the protein synthesis reactor to produce a desired protein.

2. The method as claimed in claim 1, wherein the phosphate compound is selected from the group consisting of phosphoenol pyruvate, phosphocreatine, acetyl phosphate, and polyphosphate.

3. The method as claimed in claim 1, wherein the porous solid material is selected from the group consisting of alumina, silica, and zeolites.

4. The method as claimed in claim 3, wherein the porous solid material is alumina.

5. The method as claimed in claim 1, wherein the protein synthesis reactor is operated in a mode selected from the group consisting of batch and semi-continuous modes.

6. The method as claimed in claim 1, wherein the membrane is installed at an effluent side of the reactor and an outside surface of the membrane is in contact with a solution, permitting diffusion of the solution across the membrane.

7. In a method for producing protein in a cell-free system comprising a reaction medium and a protein synthesis reactor with a membrane, the improvement comprising adding to the reaction medium a porous solid material, wherein the porous solid material has a diameter ranging from 0.1 μm to 1,000 μm and a surface area ranging from 10 m$^2$/g to 1,000 m$^2$/g.

8. The method as claimed in claim 7, wherein the porous solid material is selected from the group consisting of alumina, silica, and zeolites.

9. The method as claimed in claim 8, wherein the porous solid material is alumina.

10. The method as claimed in claim 9, wherein the alumina is present in an amount of about 30 mg/ml of reaction medium.

* * * * *